United States Patent
Nakashimada et al.

(12)

(10) Patent No.: US 6,248,314 B1
(45) Date of Patent: Jun. 19, 2001

(54) HAIR DYE COMPOSITION HAVING A PARTICULAR BUFFER CAPACITY AND CONTAINING AN ALKYLENE CARBONATE

(75) Inventors: Atsushi Nakashimada; Nozomi Nagashima; Masahiko Sakai; Hajime Miyabe; Yutaka Shibata, all of Tokyo (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 09/346,724

(22) Filed: Jul. 2, 1999

(30) Foreign Application Priority Data

Oct. 12, 1998 (JP) .................................... 10-289655
Jan. 21, 1999 (JP) .................................... 11-013048

(51) Int. Cl.⁷ ............................... A61K 7/06; A61K 7/13
(52) U.S. Cl. ...................... 424/70.11; 424/70.1; 424/401; 8/405; 8/435; 8/552; 8/562; 8/611; 8/613
(58) Field of Search .................................... 424/401, 70.1, 424/70.11, 70.13; 8/405, 435, 552, 562, 611, 613

(56) References Cited

U.S. PATENT DOCUMENTS 5,196,029  3/1993  Kawase et al. .
5,601,620  2/1997  Ishikawa .
6,096,099  *  8/2000  Kariya et al. .

FOREIGN PATENT DOCUMENTS 0 884 044  12/1998  (EP) .
0 962 216  12/1999  (EP) .

* cited by examiner

*Primary Examiner*—Thurman K. Page
*Assistant Examiner*—Brian K. Seidleck
(74) *Attorney, Agent, or Firm*—Oblon, Spivak, McClelland, Maier & Neustadt, P.C.

(57) ABSTRACT

The invention relates to a hair dye composition comprising (A) an acid dye and (B) an alkylene carbonate having 3–5 carbon atoms in total, said composition exhibiting a pH of 2–6, and having a buffer capacity of 0.007–0.5 gram equivalent/L, and to a method of dyeing hair using the hair dye composition. The hair dye composition is excellent in hair-dyeing ability without coloring the scalp and skin and has good fastness to shampoo and the like.

16 Claims, No Drawings

HAIR DYE COMPOSITION HAVING A PARTICULAR BUFFER CAPACITY AND CONTAINING AN ALKYLENE CARBONATE

TECHNICAL FIELD

The present invention relates to a hair dye composition which is excellent in hair-dyeing ability without coloring the scalp and skin and has good fastness to shampoo.

BACKGROUND ART

Acid hair dye compositions (for example, Japanese Patent Application Laid-Open Nos. 210023/1986 and 101841/1995, etc.) comprising various kinds of organic solvents represented by benzyl alcohol as a penetrant solvent have good penetrability into hair, but have involved such problems that they color the scalp and skin at the same time as hair coloring.

In order to prevent the skin from being colored, it has been conducted to reduce coloring to the skin by thickening a hair dye composition with a water-soluble polymer or the like to prevent the drooping of the hair dye composition (Japanese Patent Application Laid-Open Nos. 87450/1998, 255540/1997 and 245348/1996). However, this method has failed to essentially improve the hair dye composition. The lowering of skin-coloring tendency by analogous compounds of aromatic alcohols, lower alkylene carbonates, or the like (Japanese Patent Application Laid-Open No. 53970/1998 and Japanese Patent Publication No. 23911/1973) has also been unsatisfactory.

SUMMARY OF THE INVENTION

The present inventors have found that when an alkylene carbonate is incorporated as a penetrant solvent into an acid system containing an acid dye, and the buffer capacity of the resulting composition is adjusted to a specific range, a hair dye composition, which is excellent in hair-dyeing ability while inhibiting coloring to the skin and has good fastness to shampoo, can be obtained.

According to the present invention, there is thus provided a hair dye composition which comprises (A) an acid dye and (B) an alkylene carbonate having 3–5 carbon atoms in total, said composition exhibiting a pH of 2–6, and having a buffer capacity of 0.007–0.5 gram equivalent/L.

According to the present invention, there is also provided a method of dyeing hair which comprises applying the above hair dye composition to hair, allowing the hair to stand, washing the hair by use of a shampoo and then drying the hair.

BEST MODE FOR CARRYING OUT THE INVENTION

No particular limitation is imposed on the acid dye of the component (A) used in the present invention so far as it is a water-soluble acid dye. Examples thereof include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401.

These acid dyes may be used either singly or in any combination thereof and are preferably incorporated in a proportion of 0.001–5% by weight (hereinafter indicated merely by "%"), particularly 0.005–4%, more particularly 0.2–3% based on the total weight of the composition, from the viewpoint of practical use in that a sufficient hair-dyeing effect is achieved, and the hand skin is scarcely smeared.

The component (B) used in the present invention includes ethylene carbonate, propylenecarbonate and the like, with propylene carbonate being particularly preferred.

The component (B) is preferably incorporated in a proportion of 0.5–50%, more preferably 5–50%, particularly 10–40% based on the composition of the present invention, from the viewpoints of hair-dyeing ability and anti-coloring property to the skin.

The hair dye compositions according to the present invention must have a pH of 2–6, preferably 2–5, more preferably 2.5–4.0. If the pH is too low, the resulting composition may roughen the hair, scalp and hand skin due to an acid component in some cases. If the pH is too high, the penetration accelerating effect on the acid dye is lowered.

The hair dye compositions according to the present invention must also have a buffer capacity of 0.007–0.5 gram equivalent/L as measured in the form of a 10% aqueous solution of the composition. The buffer capacity is preferably not lower than 0.007 gram equivalent/L, but lower than 0.2 gram equivalent/L, more preferably not lower than 0.01 gram equivalent/L, but lower than 0.2 gram equivalents/L, most preferably not lower than 0.015 gram equivalent/L, but lower than 0.2 gram equivalent/L. The buffer capacity in the present invention means a value determined by using, as a measure, the concentration of a base required to raise the pH of a 10% aqueous solution of a hair dye composition at 25° C. by 1 from the initial value thereof in accordance with the following equation:

$$\text{Buffer capacity} = |dC_B/dpH|$$

wherein $C_B$ is an ion concentration of the base (gram equivalent/L).

If the buffer capacity is lower than 0.007 gram equivalent/L, no sufficient effect can be achieved from the viewpoint of hair-dyeing effect. If the buffer capacity exceeds 0.5 gram equivalent/L, no sufficient effect can be brought about from the viewpoint of coloring to the skin. It is hence not preferable for the hair dye composition to have a buffer capacity outside the above range.

Such a buffer capacity can be imparted by adding a pH buffering agent or the like to a hair dye composition. As the pH buffering agent, may be used an organic or inorganic acid and a salt thereof which exhibit a buffering action in a pH range of 2.0–6.0. As examples of the organic acid, may be mentioned citric acid, glycolic acid, succinic acid, tartaric acid, lactic acid, fumaric acid, malic acid, levulinic acid, butyric acid, valeric acid, oxalic acid, maleic acid and mandelic acid. As examples of the inorganic acid, may be mentioned phosphoric acid, sulfuric acid and nitric acid. As examples of the salt thereof, may be mentioned sodium salts, potassium salts, ammonium salts and alkanolamine salts such as triethanolamine salts. The amount of the compounds incorporated for imparting such a buffer capacity is not particularly specified and varies according to the kinds of the compounds for imparting the buffer capacity. For example, when sodium citrate is used as a compound for mainly imparting the buffer capacity, the compound is incorporated at a concentration of at least about 1%.

In the hair dye compositions according to the present invention, the incorporation of the component (B) can enhance the penetrating rate and penetration of the acid dye into hair to a degree equal to or higher than benzyl alcohol or the like which has heretofore been in common use as a penetration accelerator. In addition, although a hair dye composition making use of benzyl alcohol or the like colors the skin to such a strong extent that it cannot be removed with ease by usual washing when it comes into contact with the skin, the hair dye compositions according to the present invention, in which the component (B) is incorporated, and the buffer capacity is adjusted to the above range, feature that they scarcely color the healthy skin even when they are brought into contact with the skin though they exhibit high hair-dyeing ability. Even if the skin is colored due to reduction in the barrier capability of the skin by skin roughness or the like, or differences between individuals, the colored part can be easily cleaned by washing with soap, shampoo or the like, or so.

At this time, it is preferred to use, as a measure of the coloring of the skin, $R = \Delta E$ (pigskin)/$\Delta E$ (goat hair) which is defined as a ratio of the pigskin-coloring ability $\Delta E$ (pigskin) to the goat hair-dyeing ability $\Delta E$ (goat hair). Although there is an individual difference in both goat hair and pigskin, $\Delta E$ generally assumes values of 20–30 before coloring and 20–70 after coloring. Namely, the R value defined herein substantially assumes a value of 0.28–1. The smaller R value indicates that the skin is harder to be colored than the hair. With respect to the colorimetric values of the hair dye compositions according to the present invention, the R value can be controlled to 0.3–0.6 though it varies according to dyeing conditions. In a composition using benzyl alcohol in place of the component (B) and a composition in which the buffer capacity is not adjusted to the above-described range, this R value is 0.7–1. Therefore, according to the compositions of the present invention, the coloring of the skin can be reduced to an extent incomparable with such a composition. When such a process that the colored skin is washed with soap is conducted, the R value can be reduced to about 0.3 or so to return the skin to the state before coloring.

Into the hair dye compositions according to the present invention, one or more organic solvents selected from the group consisting of benzyloxyethanol, benzyl alcohol, phenoxyethanol, phenoxyisopropanol, methylphenoxyethanol, methylphenoxyisopropanol, benzylglycerol, N-benzylformamide, N-methylpyrrolidone, N-ethylpyrrolidone, cinnamyl alcohol, phenethyl alcohol, p-methylbenzyl alcohol, butyl cellosolve, methyl carbitol, ethyl carbitol, propyl carbitol, butyl carbitol, diethylene glycol diethyl ether and dipropylene glycol diethyl ether may be incorporated as a component (C) for the purpose of further improving hair-dyeing ability. As the organic solvent of the component (C) is preferred an analogue of an aromatic alcohol, with benzyloxyethanol or benzyl alcohol being particularly preferred. The component (C) is preferably incorporated in a proportion of 0–10%, more preferably 0.01–10%, particularly 0.1–5% based on the composition of the present invention, from the viewpoints of dyeing ability-improving effect and anti-coloring effect on the skin.

The hair dye compositions according to the present invention may further comprise (D) a water-soluble polymer for the purpose of preventing the drooping of the resulting composition upon use, and its smearing on the scalp and the like. Examples of the water-soluble polymer include gum arabic, carrageenan, karaya gum, tragacanth gum, carob gum, quince seed (marmelo), casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), poly(vinyl methyl ether) (PVM), polyvinyl pyrrolidone (PVP), sodium polyacrylate, locust bean gum, guar gum, tamarind gum, dialkyldimethylammonium cellulose sulfates, xanthan gum, alkylene oxide-modified xanthan gum, aluminum magnesium silicate and bentonite. Of these, hydroxyethyl cellulose, xanthan gum and alkylene oxide-modified xanthan gum are particularly preferred.

These water-soluble polymers may be used either singly or in any combination thereof. No limitation is imposed on the incorporating amount thereof so far as the viscosity of the resulting composition is controlled to 1,000–50,000 mPa·s. However, it is preferably incorporated in a proportion of 0.1–10%, particularly 0.5–5% based on the composition of the present invention.

Into the hair dye compositions according to the present invention, may also be incorporated a lower alcohol or polyol for the purpose of enhancing the solubility of the components (B) and (D). Specific examples thereof include those having 2 to 4 carbon atoms, such as ethanol, isopropanol, n-propanol, n-butanol, ethylene glycol, propylene glycol, isopropylene glycol, 1,3-butylene glycol and glycerol. These lower alcohols and polyols may be used either singly or in any combination thereof and are preferably incorporated in a proportion of 0.1–30%, particularly 0.1–20% based on the composition of the present invention.

Besides the above components, components commonly used in the classical cosmetic compositions and the like, for example, surfactants, cationic polymers, oily substances, silicone derivatives, perfume bases, preservatives, ultraviolet absorbents, antioxidants, germicides, propellants, etc. may further be suitably incorporated into the hair dye compositions according to the present invention so far as no detrimental influence is thereby imposed on the effects of the present invention. The hair dye compositions according to the present invention can be prepared in accordance with a method known per se in the art.

In order to use the hair dye composition according to the present invention to dye hair, it is only necessary to apply the hair dye composition to the hair, allowing the hair to stand, and then washing the hair by use of a shampoo. More specifically, a proper amount of the composition is applied to the hair with, for example, a comb or brush, and the hair thus applied is allowed to stand for about 1 to 30 minutes after the application and then washed with the shampoo. At this time, it is preferred that the hair be toweled dry after the shampooing and dried with hot air by means of a drier or the like, since color migration to clothes and the like becomes scarcely caused.

In the present invention, color migration of the hair dye component to clothes and the like can be prevented by shampooing the hair after allowed to stand. The shampoo used herein includes a shampoo comprising 5–20% of a usual anionic surfactant such as an alkylsulfate or polyoxyethylene alkylsulfate.

EXAMPLES

In the following examples, the "buffer capacity" of each composition was determined in the following manner. Namely, water was added to the composition (10 g) to 100 mL. At this time, a pH of the resultant solution was measured. A 1N aqueous solution of sodium hydroxide was then added to the solution to determine an amount (×mL) of the 1N aqueous solution of sodium hydroxide required to raise the pH of the solution of the hair dye composition by 1, thereby calculating the buffer capacity in accordance with the equation:

Buffer capacity=$X \times 10/1000$ gram equivalent/L.

Example 1

Acid hair dye compositions were prepared to conduct various tests. The formulations of the hair dye compositions used in the tests are shown in Table 1.

(1) Evaluation Methods of Hair-Dyeing Ability and Fastness to Shampoo:

Each hair dye composition (1 g) was applied to white tresses of goat hair (1 g), and the tresses were then allowed to stand for 15 minutes at 30° C. Thereafter, the tresses were washed with water, shampooed twice, rinsed once and then dried. With respect to the thus-treated tresses, 20 evaluators were got to evaluate the hair dye composition as to hair-dyeing ability to judge it in accordance with the following standard.

The tresses were then shampooed and rinsed 30 times in total and dried. With respect to the thus-treated tresses, 20 evaluators were got to evaluate the hair dye composition as to fastness to shampoo to judge it likewise in accordance with the following standard. The formulations of the shampoo and rinse used in the tests are as follows. The results are shown in Table 1.

| [Shampoo] | |
|---|---|
| Triethanolamine lauryl sulfate | 15 (wt.%) |
| Diethanolamide laurate | 1 |
| EDTA-2Na | 0.5 |
| Sodium benzoate | 0.5 |
| Water | 83 |
| [Rinse] | |
| Stearyltrimethylammonium chloride | 3 (wt.%) |
| Propylene glycol | 5 |
| Cetanol | 1.9 |
| Methylparaben | 0.1 |
| Water | 90 |

Evaluation Standard:
- ⊚: At least 80% of the evaluators evaluated that hair-dyeing ability and fastness to shampoo were good;
- ○: 50% to lower than 80% of the evaluators evaluated that hair-dyeing ability and fastness to shampoo were good;
- Δ: 20% to lower than 50% of the evaluators evaluated that hair-dyeing ability and fastness to shampoo were good;
- ×: Lower than 20% of the evaluators evaluated that hair-dyeing ability and fastness to shampoo were good.

(2) Coloring Tendency to Pigskin and Forearm, and Easiness of Washing Out:

Each hair dye composition was uniformly applied to pigskin in a proportion of 1 g per 10 cm² of the pigskin, and the pigskin was then allowed to stand at 30° C. for 15 minutes. Thereafter, the pigskin was thoroughly washed with water to sufficiently remove the hair dye composition applied to the surface thereof, and then dried. With respect to the thus-treated pigskin, 18 evaluators were got to evaluate the hair dye composition as to coloring tendency to the pigskin to judge it in accordance with the following standard.

The pigskin was further washed by scrubbing it reciprocatingly 50 times using soap, and then dried. With respect to the thus-treated pigskin,, 18 evaluators were got to evaluate the hair dye composition as to easiness of washing out to judge it likewise in accordance with the following standard. The same evaluation was also made on the human forearm. The results are shown in Table 1.

Evaluation standard:
- ⊚: At least 80% of the evaluators evaluated that no coloring of the skin weighed on their mind;
- ○: 50% to lower than 80% of the evaluators evaluated that no coloring of the skin weighed on their mind;
- Δ: 20% to lower than 50% of the evaluators evaluated that no coloring of the skin weighed on their mind;
- ×: Lower than 20% of the evaluators evaluated that no coloring of the skin weighed on their mind.

TABLE 1

| | Invention product | | | Comparative product | |
|---|---|---|---|---|---|
| | 1 | 2 | 3 | 1 | 2 |
| Black Color No. 401 | 0.1 | 0.1 | 0.1 | 0.1 | 0.1 |
| Purple Color No. 401 | 0.05 | 0.05 | 0.05 | 0.05 | 0.05 |
| Orange Color No. 205 | 0.1 | 0.1 | 0.1 | 0.1 | 0.1 |
| Benzyloxyethanol | | | | | 5 |
| Benzyl alcohol | | | 2 | 5 | |
| Ethylene carbonate | | 10 | | | |
| Propylene carbonate | 16 | 15 | 14 | | |
| Ethanol | 4 | 10 | 5 | 15 | 15 |
| Lactic acid | 3.5 | 3.5 | 3.5 | 3.5 | 3.5 |
| Caustic soda solution | Adjusted to pH 2.9 | Adjusted to pH 2.9 | Adjusted to pH 2.9 | Adjusted to pH 2.9 | Adjusted to pH 2.9 |
| Hydroxyethyl cellulose | 1.5 | 1.5 | 1.5 | 1.5 | 1.5 |
| Purified water | Balance | Balance | Balance | Balance | Balance |
| Total | 100 | 100 | 100 | 100 | 100 |
| Buffer capacity (gram equivalent/L) | 0.018 | 0.018 | 0.018 | 0.018 | 0.018 |
| Hair-dyeing ability | ○ | ⊚ | ⊚ | ○ | ○ |
| Fastness to shampoo | ○ | ○ | ⊚ | Δ | Δ |
| Difficulty of coloring pigskin | ○ | ⊚ | ⊚ | × | Δ |
| Stain after washing pigskin | ⊚ | ⊚ | ○ | Δ | Δ |

TABLE 1-continued

|  | Invention product | | | Comparative product | |
|---|---|---|---|---|---|
|  | 1 | 2 | 3 | 1 | 2 |
| Difficulty of coloring forearm | ○ | ○ | ○ | X | Δ |
| Stain after washing forearm | ◎ | ◎ | ◎ | Δ | Δ |

Example 2

Acid hair dye compositions having their corresponding compositions shown in Tables 2 and 3 were prepared, and pigskin was dyed with each of them and washed in accordance with the method set forth in Example 1(2) to conduct colorimetry and organoleptic evaluation before and after the washing. The colorimetry was conducted by means of a calorimetric color-difference meter (CR-200) manufactured by MINOLTA CO., LTD. to calculate each R value. The results are shown in Tables 2 and 3.

TABLE 2

|  | Invention product | | | Comparative product | |
|---|---|---|---|---|---|
|  | 4 | 5 | 6 | 3 | 4 |
| Black Color No. 401 | 0.1 | 0.1 | 0.1 | 0.1 | 0.1 |
| Orange Color No. 205 | 0.15 | 0.15 | 0.15 | 0.15 | 0.15 |
| Benzyloxyethanol |  |  | 2 |  | 5 |
| Benzyl alcohol |  |  |  | 5 |  |
| Ethylene carbonate |  | 10 |  |  |  |
| Propylene carbonate | 16 | 20 | 14 |  |  |
| Ethanol | 4 | 10 | 5 | 15 | 15 |
| Lactic acid | 4 | 4 | 4 | 4 | 4 |
| Caustic soda solution | Adjusted to pH 2.9 | Adjusted to pH 2.9 | Adjusted to pH 2.9 | Adjusted to pH 2.9 | Adjusted to pH 2.9 |
| Hydroxyethyl cellulose | 1.5 | 1.5 | 1.5 | 1.5 | 1.5 |
| Purified water | Balance | Balance | Balance | Balance | Balance |
| Total | 100 | 100 | 100 | 100 | 100 |
| Buffer capacity (gram equivalent/L) | 0.02 | 0.02 | 0.02 | 0.02 | 0.02 |
| R value (before washing) | 0.35 | 0.32 | 0.38 | 0.89 | 0.7 |
| Organoleptic evaluation (before washing) | ◎ | ◎ | ○ | X | Δ |
| R value (after washing) | 0.3 | 0.3 | 0.35 | 0.71 | 0.62 |
| Organoleptic evaluation (after washing) | ◎ | ◎ | ◎ | Δ | Δ |

TABLE 3

|  | Invention product | | Comp. product |
|---|---|---|---|
|  | 7 | 8 | 5 |
| Black Color No. 401 | 0.1 | 0.1 | 0.1 |
| Orange Color No. 205 | 0.15 | 0.15 | 0.15 |
| Purple Color No. 401 | 0.03 | 0.03 | 0.03 |
| Propylene carbonate | 25 | 25 | 25 |
| Ethanol | 8 | 8 | 8 |
| Citric acid | 4 | 10 | 1 |
| Caustic soda solution | Adjusted to pH 4.0 | Adjusted to pH 3.0 | Adjusted to pH 4.0 |
| Xanthan gum | 1 | 1 | 1 |
| Purified water | Balance | Balance | Balance |
| Total | 100 | 100 | 100 |
| Buffer capacity (gram equivalent/L) | 0.017 | 0.04 | 0.006 |
| R value (before washing) | 0.35 | 0.40 | 0.75 |
| Organoleptic evaluation (before washing) | ◎ | ○ | Δ |
| R value (after washing) | 0.3 | 0.35 | 0.65 |
| Organoleptic evaluation (after washing) | ◎ | ◎ | Δ |

As apparent from Tables 1 to 3, the hair dye compositions according to the present invention have excellent hair-dyeing ability and low skin-coloring tendency and can be easily washed out of the skin colored with them though they have high fastness to shampoo.

Industrial Applicability

The hair dye compositions according to the present invention are excellent in hair-dyeing ability without coloring the scalp and skin and have good fastness to shampoo.

What is claimed is:

1. A hair dye composition which comprises (A) an acid dye and (B) an alkylene carbonate having 3–5 carbon atoms in total, said composition exhibiting a pH of 2–6, and having a buffer capacity of 0.007–0.5 gram equivalent/L.

2. The hair dye composition according to claim 1, wherein the content of the alkylene carbonate having 3–5 carbon atoms in total is 0.5–50% by weight.

3. The hair dye composition according to claim 1, which further comprises an organic solvent (C) selected from the group consisting of benzyloxyethanol, benzylalcohol, phenoxyethanol, phenoxyisopropanol, methylphenoxyethanol, methylphenoxyisopropanol, benzylglycerol, N-benzylformamide, N-methylpyrrolidone, N-ethylpyrrolidone, cinnamyl alcohol, phenethyl alcohol, p-methylbenzyl alcohol, butyl cellosolve, methyl carbitol, ethyl carbitol, propyl carbitol, butyl carbitol, diethylene glycol diethyl ether, dipropylene glycol diethyl ether, and mixtures thereof.

4. The hair dye composition according to claim 1, which further comprises a water-soluble polymer (D), said composition exhibiting a viscosity of 1,000 to 50,000 mPa·s.

5. A method of dyeing hair which comprises applying to hair a hair dye composition comprising (A) an acid dye and (B) an alkylene carbonate having 3–5 carbon atoms in total, said composition exhibiting a pH of 2–6, and having a buffer capacity of 0.007–0.5 gram equivalent/L; subsequently allowing the hair to stand; and washing the hair by use of a shampoo.

6. The method according to claim 5, wherein the content of the alkylene carbonate having 3–5 carbon atoms in total is 0.5–50% by weight.

7. The method according to claim 5, wherein said composition further comprises an organic solvent (C) selected from the group consisting of benzyloxyethanol, benzyl alcohol, phenoxyethanol, phenoxyisopropanol, methylphenoxyethanol, methylphenoxyisopropanol, benzylglycerol, N-benzylformamide, N-methylpyrrolidone, N-ethylpyrrolidone, cinnamyl alcohol, phenethyl alcohol, p-methylbenzyl alcohol, butyl cellosolve, methyl carbitol, ethyl carbitol, propyl carbitol, butyl carbitol, diethylene glycol diethyl ether, dipropylene glycol diethyl ether, and mixtures thereof.

8. The method according to claim 5, wherein said composition further comprises a water-soluble polymer (D), said composition exhibiting a viscosity of 1,000 to 50,000 mPa·s.

9. The hair dye composition according to claim 2, which further comprises an organic solvent (C) selected from the group consisting of benzyloxyethanol, benzylalcohol, phenoxyethanol, phenoxyisopropanol, methylphenoxyethanol, methylphenoxyisopropanol, benzylglycerol, N-benzylformamide, N-methylpyrrolidone, N-ethylpyrrolidone, cinnamyl alcohol, phenethyl alcohol, p-methylbenzyl alcohol, butyl cellosolve, methyl carbitol, ethyl carbitol, propyl carbitol, butyl carbitol, diethylene glycol diethyl ether, dipropylene glycol diethyl ether, and mixtures thereof.

10. The hair dye composition according to claim 2, which further comprises a water-soluble polymer (D), said composition exhibiting a viscosity of 1,000 to 50,000 mPa·s.

11. The hair dye composition according to claim 3, which further comprises a water-soluble polymer (D), said composition exhibiting a viscosity of 1,000 to 50,000 mPa·s.

12. The hair dye composition according to claim 9, which further comprises a water-soluble polymer (D), said composition exhibiting a viscosity of 1,000 to 50,000 mPa·s.

13. The method according to claim 6, wherein said composition further comprises an organic solvent (C) selected from the group consisting of benzyloxyethanol, benzyl alcohol, phenoxyethanol, phenoxyisopropanol, methyl-phenoxyethanol, methylphenoxyisopropanol, benzylglycerol, N-benzylformamide, N-methylpyrrolidone, N-ethylpyrrolidone, cinnamyl alcohol, phenethyl alcohol, p-methylbenzyl alcohol, butyl cellosolve, methyl carbitol, ethyl carbitol, propyl carbitol, butyl carbitol, diethylene glycol diethyl ether, dipropylene glycol diethyl ether, and mixtures thereof.

14. The method according to claim 6, wherein said composition further comprises a water-soluble polymer (D), said composition exhibiting a viscosity of 1,000 to 50,000 mPa·s.

15. The method according to claim 7, wherein said composition further comprises a water-soluble polymer (D), said composition exhibiting a viscosity of 1,000 to 50,000 mPa·s.

16. The method according to claim 13, wherein said composition further comprises a water-soluble polymer (D), said composition exhibiting a viscosity of 1,000 to 50,000 mPa·s.

* * * * *